(12) United States Patent
Kihlberg et al.

(10) Patent No.: US 8,137,656 B2
(45) Date of Patent: Mar. 20, 2012

(54) METHOD AND APPARATUS FOR SYNTHESIS OF [$^{11}$C]PHOSGENE USING CONCENTRATED [$^{11}$C] CARBON MONOXIDE WITH UV LIGHT

(75) Inventors: Tor Kihlberg, Uppsala (SE); Tommy Ferm, Uppsala (SE); Bengt Langstrom, Uppsala (SE)

(73) Assignee: GE Healthcare Limited, Little Chalfont (GB)

( * ) Notice: Subject to any disclaimer, the term of this patent is extended or adjusted under 35 U.S.C. 154(b) by 1360 days.

(21) Appl. No.: 10/581,835

(22) PCT Filed: Nov. 29, 2004

(86) PCT No.: PCT/IB2004/003907
§ 371 (c)(1), (2), (4) Date: Jun. 5, 2006

(87) PCT Pub. No.: WO2005/054128
PCT Pub. Date: Jun. 16, 2005

(65) Prior Publication Data
US 2007/0110664 A1    May 17, 2007

(51) Int. Cl.
*A61K 51/00* (2006.01)
*A61M 36/14* (2006.01)

(52) U.S. Cl. ...................................... 424/1.11; 424/1.81

(58) Field of Classification Search ................... 424/1.81
See application file for complete search history.

(56) References Cited

U.S. PATENT DOCUMENTS

| | | | |
|---|---|---|---|
| 4,458,302 A * | 7/1984 | Shiba et al. | 362/303 |
| 5,780,860 A * | 7/1998 | Gadgil et al. | 250/432 R |
| 6,284,050 B1 * | 9/2001 | Shi et al. | 118/715 |
| 6,472,026 B1 * | 10/2002 | Maag et al. | 427/492 |
| 7,521,544 B2 * | 4/2009 | Kihlberg et al. | 534/11 |
| 2004/0197257 A1 * | 10/2004 | Kihlberg et al. | 423/418.2 |

FOREIGN PATENT DOCUMENTS

| | | |
|---|---|---|
| EP | 0282703 | 12/2002 |
| WO | 02/102711 | 12/2002 |
| WO | 2005/042441 | 5/2005 |

OTHER PUBLICATIONS

Gascard et al. (J. Phys. E: Sci. Instrum. 1982, 15, p. 627-628).*
Brinkman, G.A., et.al., "Preparation of [11C]-Phosegene" Int'l Journal of Applied Radiation and Isotopes Coden: IJaray: vol. 29, No. 11, 1978, pp. 701-702.
Patent Abstracts of Japan vol. 1998, No. 10, Aug. 31, 1998 & JP 10 135233 Sony Corp. May 22, 1998.
Diksic, Mirko, et.al.; "An on-line Synthesis of No-Carrier-Added [11C]Phosgene" Int'l Journal of Nuclear Medicine and Biology, 9(4), 283-5 Coden IJNMCI, 1982.
Roeda, D. et.al.: "A U.V.-Induced on=line Synthesis of 11C-Phosgene and the Preparation of Some of its Derivatives" Int'l Journal of Applied Radiation and Isotopes, Pergamon Press Ltd. Oxford, GB, vol. 32, 1981, pp. 931-931.
Crouzel, C.et.al., "11C-Labeled Phosgene" an Improved Procedure and Synthesis Device Int'l Journal of Applied Radiation and Isotopes, Pergamon Press, NY, NY, vol. 34, No. 11, 1983 pp. 1558-1559.
PCT/IB2004/003907 Int'l Search Report and Written Opinion dated Nov. 2005.

* cited by examiner

*Primary Examiner* — Michael G Hartley
*Assistant Examiner* — Melissa Perreira (57) ABSTRACT

Methods and systems for labeling synthesis of phosgen by UV light are provided. Methods of synthesizing labeled compounds useful as PET tracers from labeled phosgen are also provided. The resultant carbon-isotope labeled compounds are useful as radio-pharmaceuticals, especially for use in Positron Emission Tomography. Associated kits for PET studies are also provided.

6 Claims, 6 Drawing Sheets

METHOD AND APPARATUS FOR SYNTHESIS OF [$^{11}$C]PHOSGENE USING CONCENTRATED [$^{11}$C] CARBON MONOXIDE WITH UV LIGHT

FIELD OF THE INVENTION

The present invention relates to a method and an apparatus for the use of carbon-isotope monoxide in labeling synthesis. More specifically, the invention relates to a method and apparatus for producing an [$^{11}$C]carbon monoxide enriched gas mixture from an initial [$^{11}$C]carbon dioxide gas mixture, and using the produced gas mixture in labeling synthesis of phosgen by UV light. Radiolabeled phosgen is provided using radiolabeled carbon monoxide and chlorine gas as precursors.

BACKGROUND OF THE INVENTION

Tracers labeled with short-lived positron emitting radionuclides (e.g. $^{11}$C, $t_{1/2}$=20.3 min) are frequently used in various non-invasive in vivo studies in combination with positron emission tomography (PET). Because of the radioactivity, the short half-lives and the submicromolar amounts of the labeled substances, extraordinary synthetic procedures are required for the production of these tracers. An important part of the elaboration of these procedures is development and handling of new $^{11}$C-labeled precursors. This is important not only for labeling new types of compounds, but also for increasing the possibility of labeling a given compound in different positions. Throughout the development of a synthetic labeling method using short-lived radionuclides, the recognition of time as a parameter in the same category as chemical yield is important.

During the last two decades carbonylation chemistry using carbon monoxide has developed significantly. The recent development of methods such as palladium-catalyzed carbonylative coupling reactions has provided a mild and efficient tool for the transformation of carbon monoxide into different carbonyl compounds.

Carbonylation reactions using [$^{11}$C]carbon monoxide has a primary value for PET-tracer synthesis since biologically active substances often contain carbonyl groups or functionalities that can be derived from a carbonyl group. The syntheses are tolerant to most functional groups, which means that complex building blocks can be assembled in the carbonylation step to yield the target compound. This is particularly valuable in PET-tracer synthesis where the unlabeled substrates should be combined with the labeled precursor as late as possible in the reaction sequence, in order to decrease synthesis-time and thus optimize the uncorrected radiochemical yield.

When compounds are labeled with $^{11}$C, it is usually important to maximize specific radioactivity. In order to achieve this, the isotopic dilution and the synthesis time must be minimized. Isotopic dilution from atmospheric carbon dioxide may be substantial when [$^{11}$C]carbon dioxide is used in a labeling reaction. Due to the low reactivity and atmospheric concentration of carbon monoxide (0.1 ppm vs. 3.4×10$^4$ ppm for $CO_2$), this problem is reduced with reactions using [$^{11}$C] carbon monoxide.

The synthesis of [$^{11}$C]carbon monoxide from [$^{11}$C]carbon dioxide using a heated column containing reducing agents such as zinc, charcoal or molybdenum has been described previously in several publications.

The cold-trap technique is widely used in the handling of $^{11}$C-labeled precursors, particularly in the case of [$^{11}$C] carbon dioxide. The procedure has, however, only been performed in one single step and the labeled compound was always released in a continuous gas-stream simultaneous with the heating of the cold-trap. Furthermore, the volume of the material used to trap the labeled compound has been relative large in relation to the system to which the labeled compound has been transferred. Thus, the option of using this technique for radical concentration of the labeled compound and miniaturization of synthesis systems has not been explored. This is especially noteworthy in view of the fact that the amount of a $^{11}$C-labelled compound usually is in the range 20-60 nmol.

Recent technical development for the production and use of [$^{11}$C]carbon monoxide has made this compound useful in labeling synthesis. WO 02/102711 describes a system and a method for the production and use of a carbon-isotope monoxide enriched gas-mixture from an initial carbon-isotope dioxide gas mixture. [$^{11}$C]Carbon monoxide may be obtained in high radiochemical yield from cyclotron produced [$^{11}$C] carbon dioxide and can be used to yield target compounds with high specific radioactivity. This reactor overcomes the difficulties listed above and is useful in synthesis of $^{11}$C-labelled compounds using [$^{11}$C]carbon monoxide in palladium or selenium mediated reaction. With such method, a broad array of carbonyl compounds can be labeled (Kihlberg, T.; Langstrom, B. J., Org. Chem. 64, 1999, 9201-9205. Kihlberg, T.; Karimi, F.; Langstrom, B., J., Org. Chem. 67, 2002, 3687-3692).

Carbamoyl groups are common in biologically active compounds such as pharmaceuticals and are thus an important target for $^{11}$C-labeling. The selenium mediated reactions for synthesis of carbamoyl compounds are, however, limited to the use of strongly nucleophilic primary amines or favorable ring closures. [$^{11}$C]Phosgen on the other hand is very reactive and can be used to label in principle all types of carbamoyl compounds. For this reason, the use of [$^{11}$C]phosgen has been the most common approach for $^{11}$C-labeling of carbamoyl compounds.

The existing methods for [$^{11}$C]phosgen production, however, have many disadvantages. For example, [$^{11}$C]phosgen can be made in flow from [$^{11}$C]carbon monoxide with $PtCl_4$ as the chlorinating agent at elevated temperatures (Roeda, D., Crouzel, C. and Van Zanten, B., Radiochem. Radioanal. Lett., 33, 175 (1978)). However, to obtain reproducible results using this approach, temperature control is very critical and difficult, and the yield is not particularly high. In addition, it became clear that this procedure gives rise to a considerable amount of carrier phosgen, arising from inactive carbon monoxide already present in $PtCl_4$.

Another approach is described by Roeda et al (Roeda, D., Westera, G., International Journal of Applied Radiation & Isotope., 931-932, Vol. 32, 1981). It uses an in-flow [$^{11}$C] phosgen production system, using the reaction of [$^{11}$C]carbon monoxide with chlorine gas induced by UV radiation. However, this approach uses a system with a continuous gas flow with relatively large volume and amount of chlorine. The consequences are that the system is bulky and the method gives relatively low levels of specific radioactivity, since the chlorine gas seams to be a major source of carrier phosgene.

Also other methods, based on the use of [$^{11}$C]methane, suffers from low levels of specific radioactivity as well as complicated and capricious synthesis systems.

Therefore, there is a need for a system and method in order to overcome the problems listed above and provide target structures to further increase the utility of [$^{11}$C]phosgen as an important starting material in preparing useful PET tracers.

Discussion or citation of a reference herein shall not be construed as an admission that such reference is prior art to the present invention.

SUMMARY OF THE INVENTION

The present invention provides a method for labeling synthesis of phosgen, comprising:

(a) providing a UV reactor assembly comprising a reaction chamber and a UV light source, wherein the reaction chamber having a window facing the UV light source, a first gas inlet and a second gas inlet, (b) providing a reagent volume to be labeled, (c) introducing a carbon-isotope monoxide enriched gas-mixture into the reaction chamber of the UV reactor assembly via the first gas inlet, (d) introducing $Cl_2$ gas into the reaction chamber via the second gas inlet, (e) turning on the UV light source and waiting a predetermined time while the labeling synthesis occur, and (f) removing the labeled phosgen from the reaction chamber.

The present invention also provides a system for labeling synthesis, comprising: a UV reactor assembly comprising a reaction chamber and a UV light source, wherein the reaction chamber having a window facing the UV light source, a first gas inlet and a second gas inlet in a top and/or bottom surface thereof, wherein the UV light beam from the UV light source enters the window of the reaction chamber.

The present invention further provides a method for the synthesis of labeled compounds as PET tracers using [$^{11}$C]phosgen synthesized according to the method of the instant invention.

In yet another embodiment, the invention also provides $^{11}$C-labeled compounds synthesized using [$^{11}$C]phosgene produced according to the instant invention. In still another embodiment, the invention provides kits for use as PET tracers comprising such $^{11}$C-labeled compounds.

DETAILED DESCRIPTION OF THE INVENTION

The object of the invention is to provide a method and a system for production of and use of carbon-isotope monoxide in labeling synthesis that overcomes the drawbacks of the prior art devices. This is achieved by the method and system claimed in the invention.

Advantages with such a method and system is that the amount of chlorine gas can be radically decreased, and that nearly quantitative decay corrected radiochemical yields of [$^{11}$C]phosgene can be accomplished.

There are several other advantages with the present method and system. The use of a closed system consisting of materials that prevents gas diffusion, increases the stability of sensitive compounds and could be advantageous also with respect to Good Manufacturing Practice (GMP).

Still other advantages are achieved in that the resulting labeled compound is highly concentrated, and that the miniaturization of the synthesis system facilitates automation, rapid synthesis and purification, and optimization of specific radioactivity through minimization of isotopic dilution.

Embodiments of the invention will now be described with reference to the figures.

The term carbon-isotope that is used throughout this application preferably refers to $^{11}$C, but it should be understood that $^{11}$C may be substituted by other carbon-isotopes, such as $^{13}$C and $^{14}$C, if desired.

Figure 1:
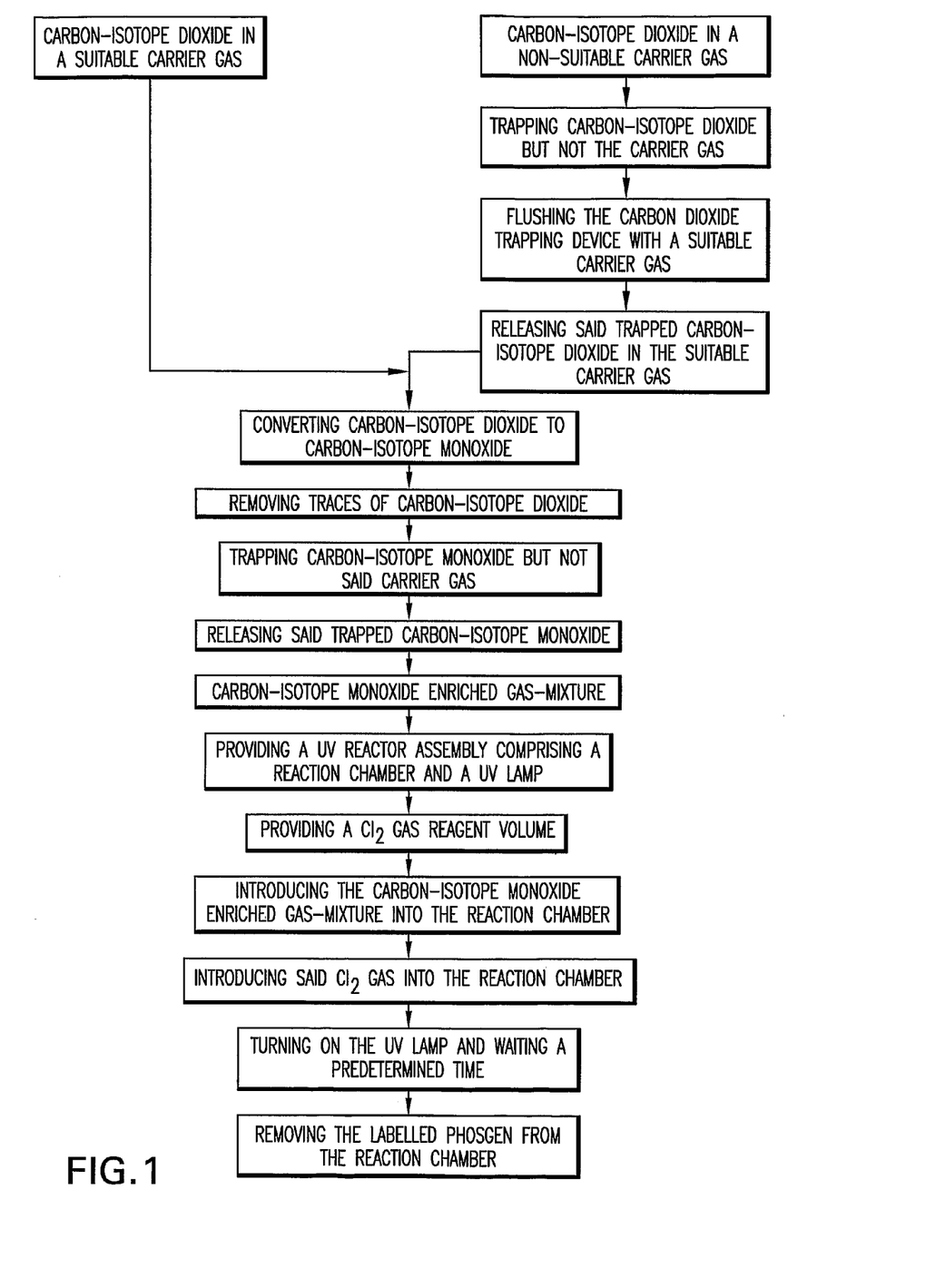
FIG. 1 shows a flow chart over the method according to the invention.

FIG. 1 shows a flow chart over the method according to the invention, which firstly comprises production of a carbon-isotope monoxide enriched gas-mixture and secondly a labeling synthesis procedure. More in detail the production part of the method comprises the steps of:

Providing carbon-isotope dioxide in a suitable carrier gas of a type that will be described in detail below.

Converting carbon-isotope dioxide to carbon-isotope monoxide by introducing said gas mixture in a reactor device which will be described in detail below.

Removing traces of carbon-isotope dioxide by flooding the converted gas-mixture through a carbon dioxide removal device wherein carbon-isotope dioxide is trapped but not carbon-isotope monoxide nor the carrier gas, The carbon dioxide removal device will be described in detail below.

Trapping carbon-isotope monoxide in a carbon monoxide trapping device, wherein carbon-isotope monoxide is trapped but not said carrier gas. The carbon monoxide trapping device will be described in detail below.

Releasing said trapped carbon-isotope monoxide from said trapping device, whereby a volume of carbon-isotope monoxide enriched gas-mixture is achieved.

The production step may further comprise a step of changing carrier gas for the initial carbon-isotope dioxide gas mixture if the initial carbon-isotope dioxide gas mixture is comprised of carbon-isotope dioxide and a first carrier gas not suitable as carrier gas for carbon monoxide due to similar molecular properties or the like, such as nitrogen. More in detail the step of providing carbon-isotope dioxide in a suitable second carrier gas such as He, Ar, comprises the steps of:

Flooding the initial carbon-isotope dioxide gas mixture through a carbon dioxide trapping device, wherein carbon-isotope dioxide is trapped but not said first carrier gas. The carbon dioxide trapping device will be described in detail below.

Flushing said carbon dioxide trapping device with said suitable second carrier gas to remove the remainders of said first carrier gas.

Releasing said trapped carbon-isotope dioxide in said suitable second carrier gas.

The labeling synthesis step that may follow the production step utilizes the produced carbon-isotope dioxide enriched gas-mixture as labeling reactant. More in detail the step of labeling synthesis comprises the steps of:

Providing a UV reactor assembly comprising a UV light source and a reaction chamber having a $Cl_2$ gas reagent inlet and a labeling reactant inlet in a top and/or bottom surface thereof. The UV reactor assembly and the reaction chamber will be described in detail below.

Providing a $Cl_2$ gas reagent volume that is to be used as reagent.

Introducing the carbon-isotope monoxide enriched gas-mixture into the reaction chamber via the labeling reactant inlet.

Introducing said $Cl_2$ gas reagent into the reaction chamber via the $Cl_2$ gas reagent inlet.

Turning on the UV light source and waiting a predetermined time while the labeling synthesis occurs.

Removing the labeled phosgene from the reaction chamber.

The step of waiting a predetermined time may further comprise adjusting the temperature of the reaction chamber such that the labeling synthesis is enhanced.

Figure 2:
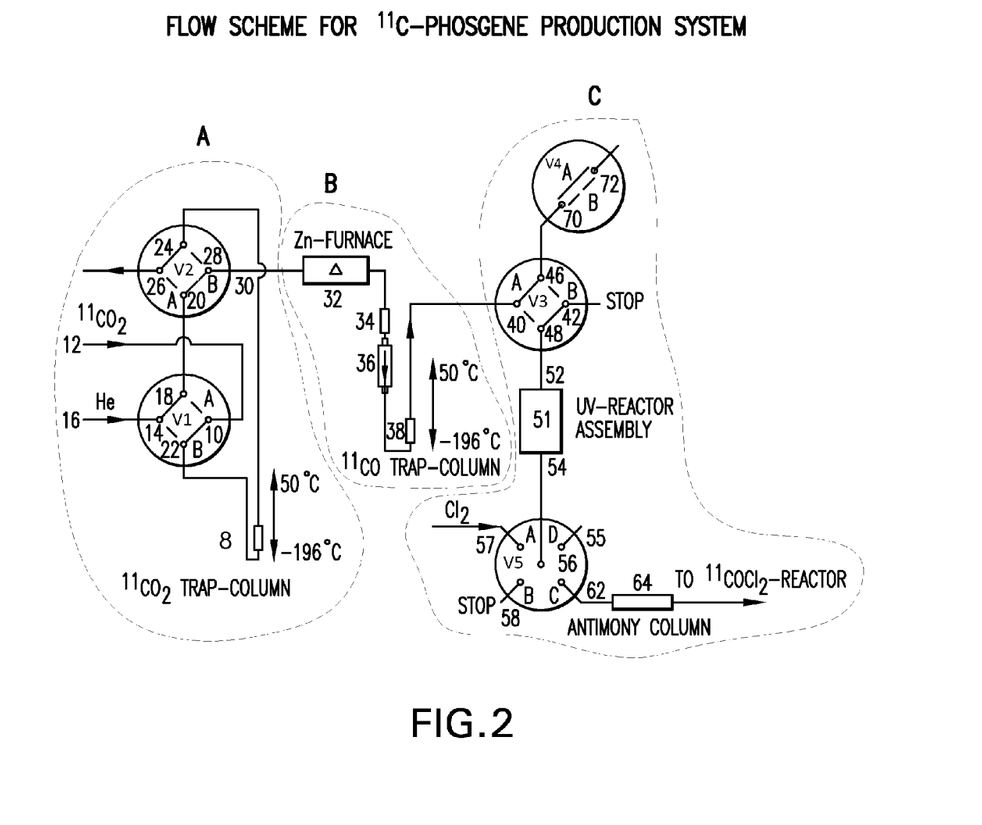
FIG. 2 is a schematic view of a carbon-isotope monoxide production and labeling-system according to the invention.

FIG. 2 schematically shows a [$^{11}$C]carbon dioxide production and labeling-system according to the present invention. The system is comprised of three main blocks, each handling one of the three main steps of the method of production and labeling:

Block A is used to perform a change of carrier gas for an initial carbon-isotope dioxide gas mixture, if the initial carbon-isotope dioxide gas mixture is comprised of carbon-isotope dioxide and a first carrier gas not suitable as carrier gas for carbon monoxide.

Block B is used to perform the conversion from carbon-isotope dioxide to carbon-isotope monoxide, and purify and concentrate the converted carbon-isotope monoxide gas mixture.

Block C is used to perform the carbon-isotope phosgene synthesis.

Block A is normally needed due to the fact that carbon-isotope dioxide usually is produced using the $14N(p,\alpha)^{11}C$ reaction in a target gas containing nitrogen and 0.1% oxygen, bombarded with 17 MeV protons, whereby the initial carbon-isotope dioxide gas mixture comprises nitrogen as carrier gas. However, compared with carbon monoxide, nitrogen show certain similarities in molecular properties that makes it difficult to separate them from each other, e.g. in a trapping device or the like, whereby it is difficult to increase the concentration of carbon-isotope monoxide in such a gas mixture. Suitable carrier gases may instead be helium, argon or the like. Block A can also used to change the pressure of the carrier gas (e.g. from 1 to 4 bar), in case the external system does not tolerate the gas pressure needed in block B and C. In an alternative embodiment the initial carbon-isotope dioxide gas mixture is comprised of carbon-isotope dioxide and a first carrier gas that is well suited as carrier gas for carbon monoxide, whereby the block A may be simplified or even excluded.

According to a preferred embodiment (FIG. 2), block A is comprised of a first valve V1, a carbon dioxide trapping device 8, and a second valve V2.

The first valve V1 has a carbon dioxide inlet 10 connected to a source of initial carbon-isotope dioxide gas mixture 12, a carrier gas inlet 14 connected to a source of suitable carrier gas 16, such as helium, argon and the like. The first valve V1 further has a first outlet 18 connected to a first inlet 20 of the second valve V2, and a second outlet 22 connected to the carbon dioxide trapping device 8. The valve V1 may be operated in two modes A, B, in mode A the carbon dioxide inlet 10 is connected to the first outlet 18 and the carrier gas inlet 14 is connected to the second outlet 22, and in mode B the carbon dioxide inlet 10 is connected to the second outlet 22 and the carrier gas inlet 14 is connected to the first outlet 18.

In addition to the first inlet 20, the second valve V2 has a second inlet 24 connected to the carbon dioxide trapping device 8. The second valve V2 further has a waste outlet 26, and a product outlet 28 connected to a product inlet 30 of block B. The valve V2 may be operated in two modes A, B, in mode A the first inlet 20 is connected to the waste outlet 26 and the second inlet 24 is connected to the product outlet 28, and in mode B the first inlet 20 is connected to the product outlet 28 and the second inlet 24 is connected to the waste outlet 26.

The carbon dioxide trapping device 8 is a device wherein carbon dioxide is trapped but not said first carrier gas, which trapped carbon dioxide thereafter may be released in a controlled manner. This may preferably be achieved by using a cold trap, such as a column containing a material which in a cold state, (e.g. −196° C. as in liquid nitrogen or −186° C. as in liquid argon) selectively trap carbon dioxide and in a warm state (e.g. +50° C.) releases the trapped carbon dioxide. (In this text the expression "cold trap" is not restricted to the use of cryogenics. Thus, materials that traps the topical compound at room temperature and release it at a higher temperature are included). Examples of suitable material are silica and porapac Q®. The trapping behavior of a silica-column or a porapac-column is related to dipole-dipole interactions or possibly Van der Waal interactions. The said column 8 is preferably formed such that the volume of the trapping material is to be large enough to efficiently trap (>95%) the carbon-isotope dioxide, and small enough not to prolong the transfer of trapped carbon dioxide to block B. In the case of porapac Q® and a flow of 100 ml nitrogen/min, the volume should be 50-150 µl. The cooling and heating of the carbon dioxide trapping device 8 may further be arranged such that it is performed as an automated process, e.g. by automatically lowering the column into liquid nitrogen and moving it from there into a heating arrangement.

According to the preferred embodiment of FIG. 2, block B is comprised of a reactor device 32 in which carbon-isotope dioxide is converted to carbon-isotope monoxide, a carbon dioxide removal device 34, a check-valve 36, and a carbon monoxide trapping device 38, which all are connected in a line.

In the preferred embodiment the reactor device 32 is a reactor furnace comprising a material that when heated to the right temperature interval converts carbon-isotope dioxide to carbon-isotope monoxide. A broad range of different materials with the ability to convert carbon dioxide into carbon monoxide may be used, e.g. zinc or molybdenum or any other element or compound with similar reductive properties. If the reactor device 32 is a zinc furnace it should be heated to a temperature between 350° C. and 400° C., and it is important that the temperature is regulated with high precision. The melting point of zinc is 420° C. and the zinc-furnace quickly loses it ability to transform carbon dioxide into carbon monoxide when the temperature reaches over 410° C., probably due to changed surface properties. The material should be efficient in relation to its amount to ensure that a small amount can be used, which will minimize the time needed to transfer radioactivity from the carbon dioxide trapping device 8 to the subsequent carbon monoxide trapping device 38. The amount of material in the furnace should be large enough to ensure a practical life-time for the furnace (at least several days). In the case of zinc granulates, the volume should be 100-1000 µl.

The carbon dioxide removal device 34 is used to remove traces of carbon-isotope dioxide from the gas mixture exiting the reactor device 32. In the carbon dioxide removal device 34, carbon-isotope dioxide is trapped but not carbon-isotope monoxide nor the carrier gas. The carbon dioxide removal device 34 may be comprised of a column containing Ascarite® (i.e. sodium hydroxide on silica). Carbon-isotope dioxide that has not reacted in the reactor device 32 is trapped in this column (it reacts with sodium hydroxide and turns into sodium carbonate), while carbon-isotope monoxide passes through. The radioactivity in the carbon dioxide removal device 34 is monitored as a high value indicates that the reactor device 32 is not functioning properly.

Like the carbon dioxide trapping device 8, the carbon monoxide trapping device 38, has a trapping and a releasing state. In the trapping state carbon-isotope monoxide is selectively trapped but not said carrier gas, and in the releasing state said trapped carbon-isotope monoxide is released in a controlled manner. This may preferably be achieved by using a cold trap, such as a column containing silica or materials of similar properties, such as molecular sieves. Such a cold trap selectively traps carbon monoxide in a cold state below −100° C., e.g. −196° C. as in liquid nitrogen or −186° C. as in liquid argon, and releases the trapped carbon monoxide in a warm state (e.g. +50° C.). The trapping behavior of the silica-column is related to dipole-dipole interactions or possibly Van der Waal interactions. The ability of the silica-column to trap carbon-isotope monoxide is reduced if the helium, carrying the radioactivity, contains nitrogen. A rationale is that since the physical properties of nitrogen are similar to carbon monoxide, nitrogen competes with carbon monoxide for the trapping sites on the silica.

According to the preferred embodiment of FIG. 2, block C is comprised of a first and a second reaction chamber valve V3 and V5, a vent/stop valve V4 and the UV reactor assembly 51 which comprises a UV light source 91 and a reaction chamber 50.

The first reaction chamber valve V3 has a gas mixture inlet 40 connected to the carbon monoxide trapping device 38, a stop position 42, a waste outlet 46, and a reaction chamber connection port 48 connected to a first gas inlet 52 of the reaction chamber 50. The first reaction chamber valve V3 has two modes of operation A and B. In mode A, gas mixture inlet 40 is connected to waste outlet 46 and stop position 42 is connected to reaction chamber connection port 48. In mode B, stop position 42 is connected with waste outlet 46 and gas mixture inlet 40 is connected to reaction chamber connection port 48.

The vent/stop valve V4 has an inlet 70 connected to reaction chamber valve V3, and an outlet 72. The vent/stop valve has two modes of operation A and B. In mode A, inlet 70 and outlet 72 are connected. In mode B, inlet 70 and outlet 72 are disconnected.

Figure 3:
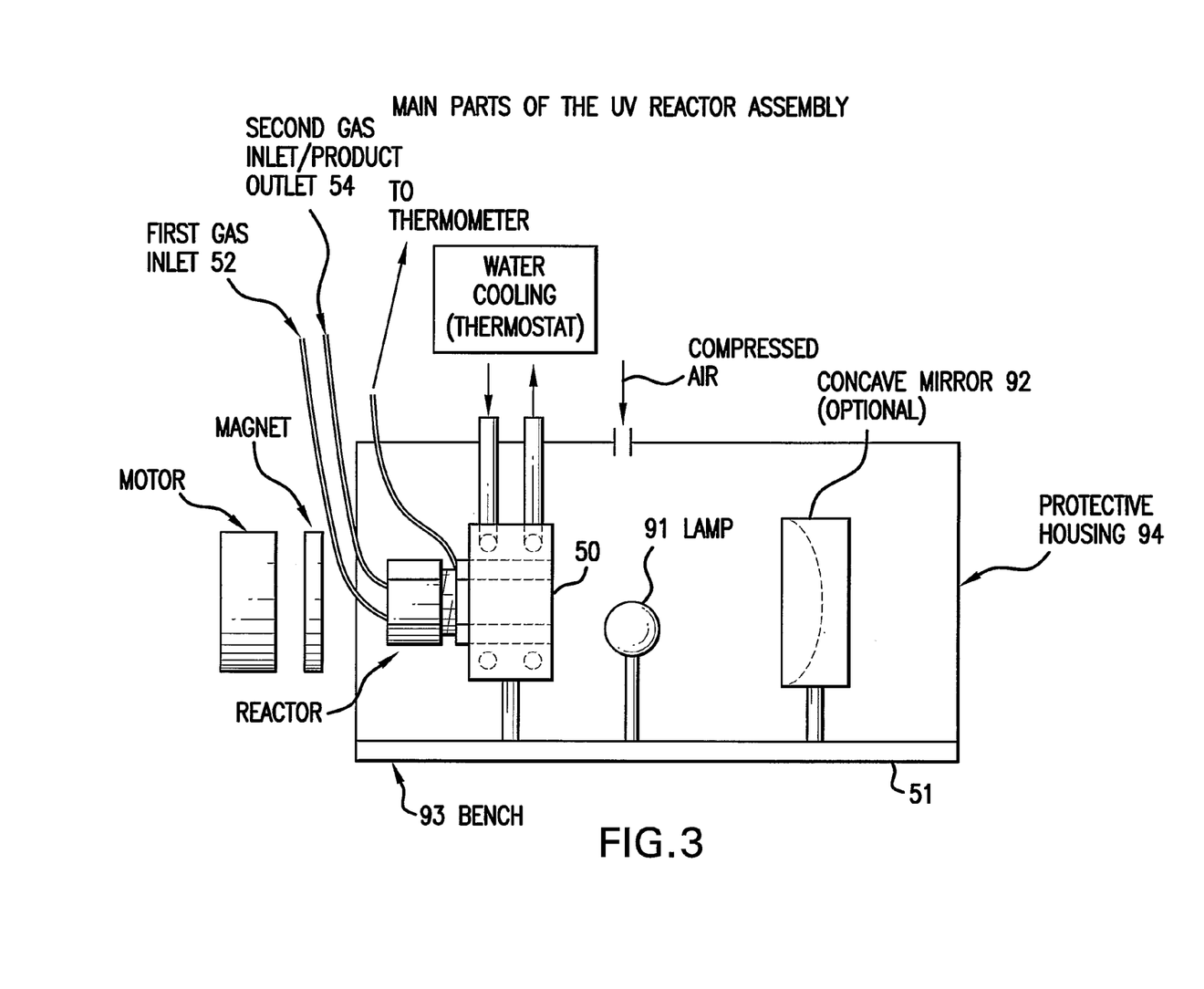
FIG. 3 shows the main parts of the UV reactor assembly.

FIG. 3 is a diagram of UV reactor assembly 51. It comprises of a UV light source 91 and a reaction chamber 50. Suitable UV light source may be a UV lamp in the vicinity of the reactor or a setup including a UV lamp, an optical focus system and an optical fiber that guides the UV light to the reactor window. In a preferred embodiment, it also includes a bench 93 and protective housing 94, so that all parts located inside of the protective housing and mounted on the bench. Optionally, it may include a concave mirror 92 so that the UV beam may be focused. In the most preferred embodiment, it further comprises a motor 95, a magnet stirrer 96, a magnet stirring bar 97 and a thermocouple 98 (see FIG. 5).

In a preferred embodiment, all parts are mounted on a bench. They are shielded with a thin protective housing outside for protection against UV radiation. Compressed air is supplied through inlet attached to the top face of the housing to ventilate the device and to provide normal operation conditions for the UV light source.

Figure 4:
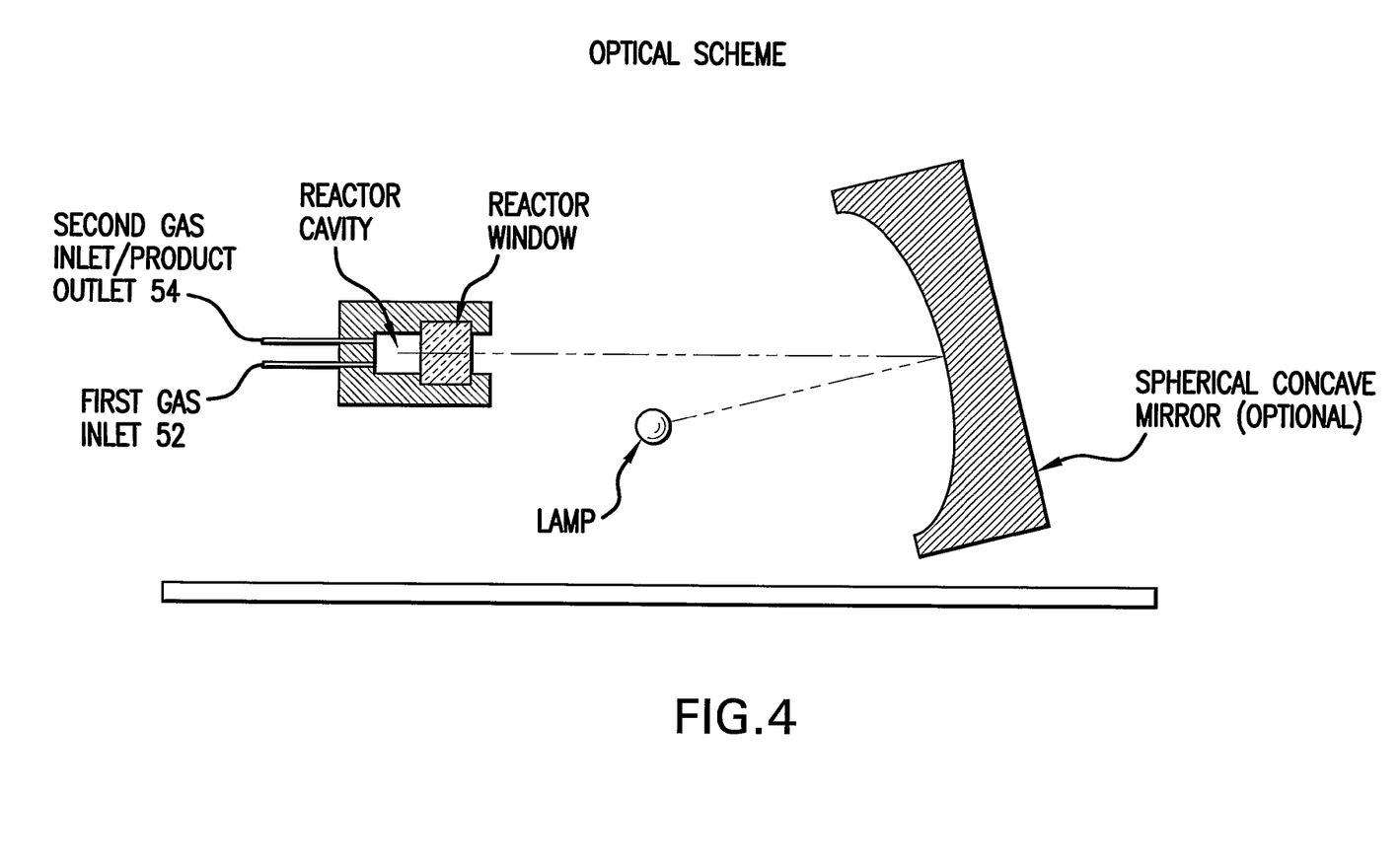
FIG. 4 is the schematic diagram of the optical scheme of the UV reactor assembly.

An optical scheme is illustrated in FIG. 4. The UV light beam from the UV light source may be directed directly to the reactor cavity, or as an alternative embodiment, an optional spherical concave mirror may be used to collect the output of the arc and direct it onto the reactor cavity. When a spherical concave mirror is used, the light source and reactor are displaced from the optical axis of the mirror so that the UV light source does not block the light collected by the mirror. This also prevents the bulb from overheating when a UV lamp is used. The distance between the reactor and the UV light source is kept at minimum to ensure a minimal arc image.

The reaction chamber 51 has a first gas inlet 52 and a second gas inlet 54, which are arranged such that they terminate at the top and/or bottom surface of the chamber. The second gas inlet 54 may also be used as product outlet after the labeling is finished. During operation the carbon-isotope monoxide enriched gas mixture is introduced into the reaction chamber 51 through the first gas inlet 52, where after $Cl_2$ gas enters the reaction chamber 51 through the second gas inlet 54. After the labeling is finished the labeled volume is nearly quantitatively transferred from the reaction chamber with a carrier gas, such as helium, via the second gas inlet/product outlet 54, with the first reaction chamber valve V3 in mode B, and the second reaction chamber valve V5 in mode C.

Figure 5:
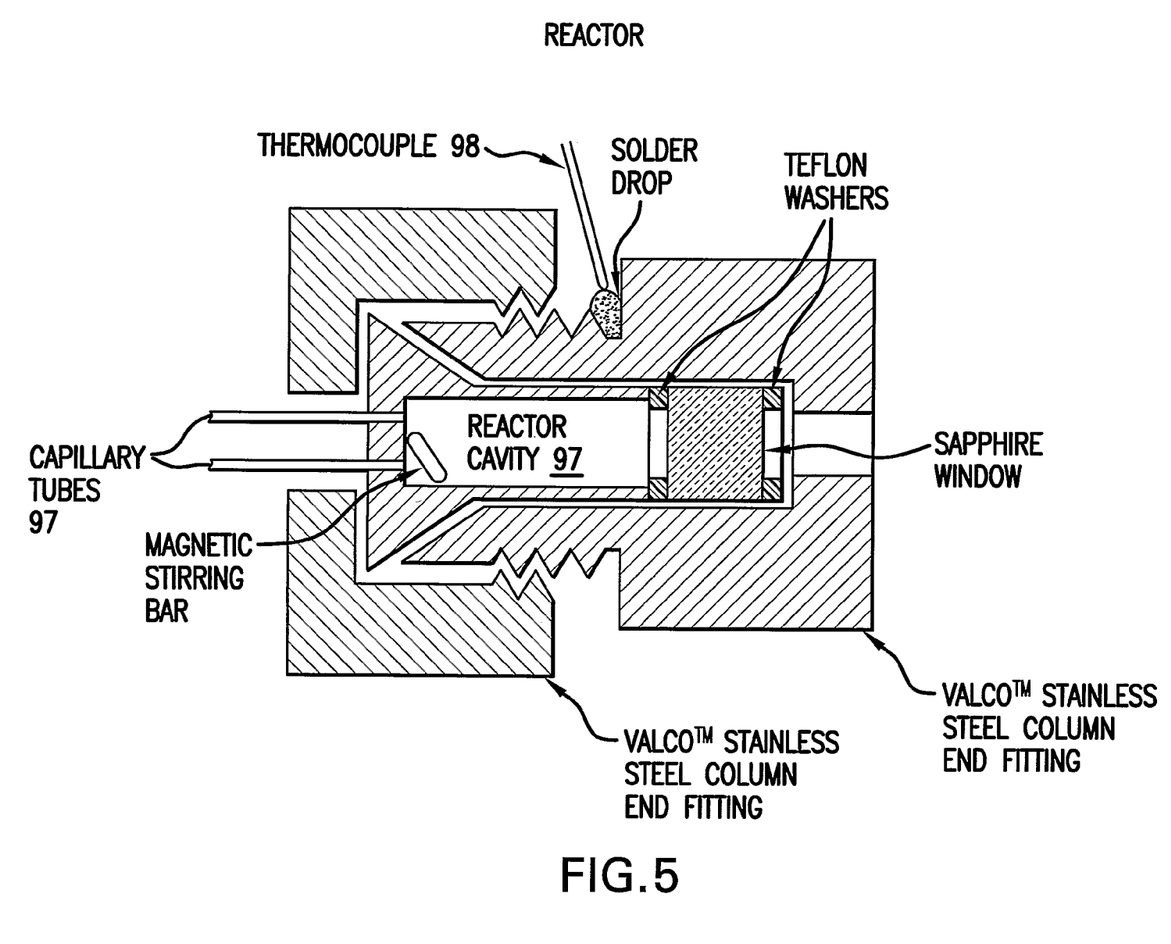
FIG. 5 is the cross-sectional view of the reaction chamber.

In a specific embodiment, FIG. 5 shows a reaction chamber made from stainless steel (Valco™) column end fitting. It is equipped with sapphire window, which is a hard material transparent to short wavelength UV radiation. The window is pressed between two Teflon washers inside the drilled column end fitting to make the reactor tight. Temperature measurement can be accomplished with the thermocouple 98 attached by solder drop to the outer side of the reactor. The magnet stirrer drives small Teflon coated magnet place inside the reaction chamber. The magnetic stirrer can be attached to the side of the reaction chamber in the assembly. Distance between the magnet stirrer and the reactor should be minimal.

Figure 6:
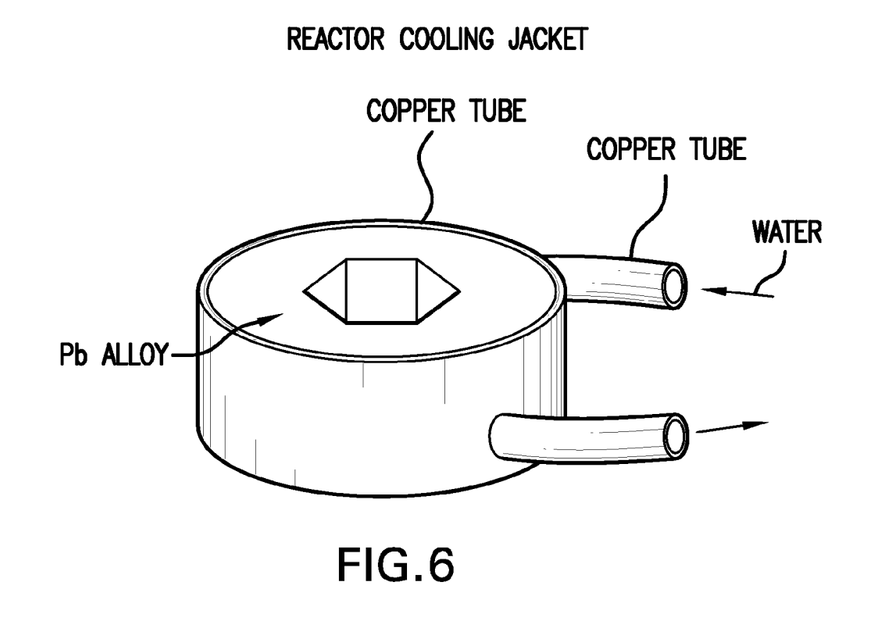
FIG. 6 shows reaction chamber and its cooling jacket.

FIG. 6 illustrates a device used to remove excessive heat produced by the light source and keep the reaction chamber at constant temperature. Copper tube can be placed into the short piece of copper tube of larger diameter filled up with lead alloy. Hexagonal hole can be made to fit the reaction chamber nut tightly. To increase heat transfer between reactor and the thermostat, thermoconductive silicon grease can be used. The thermostat can then be connected to standalone water bath thermostat with rubber tubes.

Referring back to FIG. 2, the second reaction chamber valve V5 has a $Cl_2$ gas inlet 57, a stop 58, an outlet 62 to antimony column 64, and a port 55. The second reaction chamber valve V4 has four modes of operation A to D. The reaction chamber connection port 56 is: in mode A connected to the $Cl_2$ gas inlet 57, in mode B it is connected to the stop 58, in mode C it is connected to the outlet 62 and in mode D it is connected to port 55.

Except for the small volume of silica in the carbon monoxide trapping devise 38, an important difference in comparison to the carbon dioxide trapping device 8, as well as to all related prior art, is the procedure used for releasing the carbon monoxide. After the trapping of carbon monoxide on carbon monoxide trapping devise 8, valve V4 is changed from mode A to B to stop the flow from the carbon monoxide trapping devise 38 and increase the gas-pressure on the carbon monoxide trapping devise 38 to the set feeding gas pressure (3-5 bar). The carbon monoxide trapping devise 38 is then heated to release the carbon monoxide from the silica surface while not significantly expanding the volume of carbon monoxide in the carrier gas. Valve V3 is changed from mode A to B. At this instance the carbon monoxide is rapidly and almost quantitatively transferred in a well-defined micro-plug into the reaction chamber 50. Micro-plug is defined as a gas volume less than 10% of the volume of the reaction chamber 50, containing the topical substance (e.g. 1-20 μL). This unique method for efficient mass-transfer to a small reaction chamber 50, having a closed outlet, has the following prerequisites:

A micro-column 38 defined as follows should be used. The volume of the trapping material (e.g. silica) should be large enough to efficiently trap (>95%) the carbon-isotope monoxide, and small enough (<1% of the volume of a subsequent reaction chamber 50) to allow maximal concentration of the carbon-isotope monoxide. In the case of silica and a reaction chamber 50 volume of 200 the silica volume should be 0.1-2 μl.

The dead volumes of the tubing and valve(s) connecting the silica column and the reaction chamber 50 should be minimal (<10% of the micro-autoclave volume).

The pressure of the carrier gas should be 3-5 times higher than the pressure in the reaction chamber 50 before transfer (1 atm.).

In one specific preferred embodiment specifications, materials and components are chosen as follows. High pressure valves from Valco®, Reodyne® or Cheminert® are used. Stainless steel tubing with o.d. 1/16" is used except for the connections to the silica or porapac-column 8, the silica-column 38 and the reaction chamber 50 where stainless steel tubing with o.d. 1/32" are used in order to facilitate the translation movement. The connections between V1, V2 and V3 should have an inner diameter of 0.2-1 mm. The requirement is that the inner diameter should be large enough not to obstruct the possibility to achieve the optimal flow of He (2-50 ml/min) through the system, and small enough not to prolong the time needed to transfer the radioactivity from the silica or porapac-column 8 to the silica-column 38. The dead volume of the connection between V3 and the autoclave should be minimized (<10% of the autoclave volume). The inner diameter (0.05-0.1 mm) of the connection must be large enough to allow optimal He flow (2-50 ml/min). The dead volume of the connection between V3 and reactor 51 should be less than 10% of the autoclave volume.

When column 8 is a porapac-column, it is preferably comprised of a stainless steel tube (o.d.=1/8", i.d.=2 mm, l=20 mm) filled with Porapac Q® and fitted with stainless steel screens. The silica-column 38 preferably is comprised of a stainless steel tube (o.d=1/16", i.d.=0.1 mm) with a cavity (d=1 mm, h=1 mm, V=0.8 μl) in the end. The cavity is filled with silica powder (100/80 mesh) of GC-stationary phase type. The end of the column is fitted against a stainless steel screen.

The antimony column 64 has an inlet and an outlet and is comprised of a tube made of materials that are inert to $Cl_2$ gas. The column is filled with 50-1000 mg granular antimony (e.g. 10-50 mesh), enough to consume the surplus of $Cl_2$ gas. The antimony can be kept at place with two frits.

It should be noted that a broad range of different materials could be used in the [$^{11}$C]carbon dioxide and [$^{11}$C]carbon monoxide trapping devices. If a GC-material is chosen, the criterions should be good retardation and good peak-shape for carbon dioxide and carbon monoxide respectively. The latter will ensure optimal recovery of the radioactivity.

Below a detailed description is given of a method of producing carbon-isotope using an exemplary system as described above.

Preparations of the system are performed by the steps 1 to 5:
1. V1 in position A, V2 in position A, V3 in position A, V4 in position A, V3 in position B, V5 in position C, helium flow on with a max pressure of 5 bar. With this setting, the helium flow goes through the [$^{11}$C]carbon dioxide trapping column, the zinc furnace, the [$^{11}$C]carbon monoxide trapping column, the reaction chamber 54, and the antimony column. The system is conditioned with helium and it can be checked that helium can be flowed through the system with at least 10 ml/min.
2. The zinc-furnace is turned on and set at 360-400° C.
3. The [$^{11}$C]carbon dioxide and the [$^{11}$C]carbon monoxide trapping columns are cooled with liquid nitrogen. At −196° C., [$^{11}$C]carbon dioxide trapping column and the [$^{11}$C]carbon monoxide trapping column efficiently traps carbon-isotope dioxide and carbon-isotope monoxide respectively.
4. V3 in position A and then V5 in position A. Reactor 54 is now loaded with chlorine gas.
5. V5 in position B (stop).

Production of carbon-isotope dioxide may be performed by the steps 6 to 7:
6. Carbon-isotope dioxide is produced using the 14N(p,α) $^{11}$C reaction in a target gas containing nitrogen (AGA, Nitrogen 6.0) and 0.1% oxygen (AGA. Oxygen 4.8), bombarded with 17 MeV protons.
7. The carbon-isotope dioxide is transferred to the apparatus using nitrogen with a flow of 100 ml/min.

Synthesis of carbon-isotope phosgen may thereafter be performed by the steps 8 to 14:
8. V1 in position B and V2 in position B. The nitrogen flow containing the carbon-isotope dioxide is now directed through the [$^{11}$C]carbon dioxide trapping column (cooled to −196° C.) and out through a waste line. The radioactivity trapped in the [$^{11}$C]carbon dioxide trapping column is monitored.
9. When the radioactivity has peaked, V1 is changed to position A. Now a helium flow is directed through the [$^{11}$C]carbon dioxide trapping column and out through the waste line (26). By this operation the tubings and the [$^{11}$C]carbon dioxide trapping column are rid of nitrogen.
10. V2 in position A and the [$^{11}$C]carbon dioxide trapping column is warmed to about 50° C. The radioactivity is now released from the [$^{11}$C]carbon dioxide trapping column and transferred with a helium flow of 10 ml/min into the zinc-furnace where it is transformed into carbon-isotope monoxide.
11. Before reaching the [$^{11}$C]carbon monoxide trapping column (cooled to −196° C.), the gas flow passes the ascarite-column. The carbon-isotope monoxide is now trapped on the [$^{11}$C]carbon monoxide trapping column. The radioactivity in the [$^{11}$C]carbon monoxide trapping column is monitored and when the value has peaked, V4 is set to position B.
12. The [$^{11}$C]carbon monoxide trapping column is heated to approximately 50° C., which releases the carbon-isotope monoxide. V3 is set to position B and the carbon-isotope monoxide is transferred to the reaction chamber 54 within 15 s.
13. V3 is set to position A, and the reactor 54 is irradiated with UV-light.
14. After a sufficient reaction-time (10 s-2 min), V5 is set to position C and then V3 is set to position B. The content of the reaction chamber 50 is transferred via the antimony column to a compartment where the [$^{11}$C]phosgene is trapped and used in a labeling reaction.

With the recently developed fully automated version of the reaction chamber 50 system according to the invention, the value of [$^{11}$C]carbon monoxide as a precursor for $^{11}$C-labelled tracers has become comparable with [$^{11}$C]methyl iodide. Currently, [$^{11}$C]methyl iodide is the most frequently used $^{11}$C-precursor due to ease in production and handling and since groups suitable for labeling with [$^{11}$C]methyl iodide (e.g. hetero atom bound methyl groups) are common among biologically active substances. Phosgene, which can be conveniently synthesized and labeled with [$^{11}$C]carbon monoxide, is also an important starting material in synthesizing biologically active substances. In many cases, this approach may even be more advantageous. The use of [$^{11}$C] carbon monoxide and [$^{11}$C]phosgene for production of PET-tracers may thus become an interesting complement to [$^{11}$C] methyl iodide. Furthermore, through the use of similar technology, this method will most likely be applicable for synthesis of $^{13}$C and $^{14}$C substituted compounds.

The main advantage of the present invention is to provide a compact and efficient system and method for synthesizing [$^{11}$C]phosgene with high specific radioactivity. [$^{11}$C]Phosgene thus synthesized may react with a number of substrates to give useful $^{11}$C-labeled products useful as valuable PET tracers. A general reaction scheme is illustrated as follows:

* = $^{11}$C wherein X is selected from N, O, S or Se, and R, R', R" and R'" are independently void, H, linear or cyclic lower alkyl or substituted alkyl, aryl or substituted aryl, and may contain carbonyl, hydroxy, thiol, halogen, nitrile, isonitrile, cyanate, isocyanate, thiocyanate, isothiocyanate functional groups, carbon-carbon double bonds or carbon-carbon triple bonds. Further R, R', R" and R'" can be connected in the case of ring closure reactions. The resultant labeled product have a formula, wherein X, R, R', R" and R" are defined as above. They provide valuable PET tracers for various PET studies. Examples of the resultant labeled products include [$^{11}$C] LU29-066, [$^{11}$C] and [$^{11}$C]urea. In an embodiment of the present invention, it provides a method of using these labeled products as PET tracers for use in PET imaging. In another embodiment of the present invention, it provides kits for use as PET tracers comprising a resultant $^{11}$C-labeled product.

Such kits are designed to give sterile products suitable for human administration, e.g. direct injection into the bloodstream. Suitable kits comprise containers (e.g. septum-sealed vials) containing the adrenergic interfering agent and precursor of the adrenergic imaging agent.

The kits may optionally further comprise additional components such as radioprotectant, antimicrobial preservative, pH-adjusting agent or filler.

By the term "radioprotectant" is meant a compound which inhibits degradation reactions, such as redox processes, by trapping highly-reactive free radicals, such as oxygen-containing free radicals arising from the radiolysis of water. The radioprotectants of the present invention are suitably chosen from: ascorbic acid, para-aminobenzoic acid (i.e. 4-aminobenzoic acid), gentisic acid (i.e. 2,5-dihydroxybenzoic acid) and salts thereof with a biocompatible.

By the term "antimicrobial preservative" is meant an agent which inhibits the growth of potentially harmful micro-organisms such as bacteria, yeasts or moulds. The antimicrobial preservative may also exhibit some bactericidal properties, depending on the dose. The main role of the antimicrobial preservative(s) of the present invention is to inhibit the growth of any such micro-organism in the pharmaceutical composition post-reconstitution, i.e. in the radioactive diagnostic product itself. The antimicrobial preservative may, however, also optionally be used to inhibit the growth of potentially harmful micro-organisms in one or more components of the kit of the present invention prior to reconstitution. Suitable antimicrobial preservatives include: the parabens, i.e. methyl, ethyl, propyl or butyl paraben or mixtures thereof; benzyl alcohol; phenol; cresol; cetrimide and thiomersal. Preferred antimicrobial preservative(s) are the parabens.

The term "pH-adjusting agent" means a compound or mixture of compounds useful to ensure that the pH of the reconstituted kit is within acceptable limits (approximately pH 4.0 to 10.5) for human administration. Suitable such pH-adjusting agents include pharmaceutically acceptable buffers, such as tricine, phosphate or TRIS [i.e. tris(hydroxymethyl)aminomethane], and pharmaceutically acceptable bases such as sodium carbonate, sodium bicarbonate or mixtures thereof. When the ligand conjugate is employed in acid salt form, the pH-adjusting agent may optionally be provided in a separate vial or container, so that the user of the kit can adjust the pH as part of a multi-step procedure.

By the term "filler" is meant a pharmaceutically acceptable bulking agent which may facilitate material handling during production and lyophilisation. Suitable fillers include inorganic salts such as sodium chloride, and water soluble sugars or sugar alcohols such as sucrose, maltose, mannitol or trehalose.

EXAMPLES

The invention is further described in the following example which is in no way intended to limit the scope of the invention.

Example

Experimental Setup

[$^{11}$C]Carbon dioxide production was performed using a Scanditronix MC-17 cyclotron at Uppsala IMANET. The $^{14}$N(p,α)$^{11}$C reaction was employed in a gas target containing nitrogen (Nitrogen 6.0) and 0.1% oxygen (Oxygen 4.8) which was bombarded with 17 MeV protons.

[$^{11}$C]Carbon monoxide was obtained by reduction of [$^{11}$C] carbon dioxide as described in the instant application.

The syntheses with [$^{11}$C]carbon dioxide were performed with an automated module as part of the system "Synthia 2000".

Specific Embodiments

Citation of References

The present invention is not to be limited in scope by specific embodiments described herein. Indeed, various modifications of the inventions in addition to those described herein will become apparent to these skilled in the art from the foregoing description and accompanying figures. Such modifications are intended to fall within the scope of the appended claims.

Various publications and patent applications are cited herein, the disclosures of which are incorporated by reference in their entireties.

What is claimed is:

1. A method for labeling synthesis of phosgene, comprising:
   (a) providing a UV reactor assembly comprising a high pressure reaction chamber and a UV light source, wherein the high pressure reaction chamber comprising a window facing a concave minor, a first gas inlet and a second gas inlet,
   (b) introducing a carbon-isotope monoxide enriched gas-mixture into the reaction chamber of the UV reactor assembly via the first gas inlet, (c) introducing $Cl_2$ gas into the reaction chamber via the second gas inlet to obtain a $Cl_2$-carbon-isotope monoxide gas mixture, (d) irradiating the $Cl_2$-carbon-isotope monoxide gas mixture with UV light for an amount of time sufficient to promote the labeling synthesis, and (e) removing the labeled phosgene from the reaction chamber.

2. A method of claim 1, wherein the carbon-isotope is $^{11}C$, $^{13}C$, or $^{14}C$.

3. A method of claim 1, wherein the carbon-isotope is $^{11}C$.

4. A method of claim 1, wherein the UV light source is a UV lamp.

5. A method of claim 1, further comprising stirring the $Cl_2$-carbon-isotope monoxide gas mixture during the irradiating step.

6. A method of claim 1, further comprising adjusting the temperature of the reaction chamber during the irradiating step.

* * * * *